United States Patent [19]

Lundy et al.

[11] Patent Number: 5,716,939
[45] Date of Patent: Feb. 10, 1998

[54] AMIDE DERIVATIVES OF 16-MEMBERED RING ANTIBIOTIC MACROLIDES

[75] Inventors: Kristin Marie Lundy, Groton, Conn.; Chi B. Vu, Chestnut Hill, Mass.

[73] Assignee: Pfizer Inc., New York, N.Y.

[21] Appl. No.: 557,170

[22] PCT Filed: Jul. 4, 1994

[86] PCT No.: PCT/IB94/00199
  § 371 Date: Dec. 22, 1995
  § 102(e) Date: Dec. 22, 1995

[87] PCT Pub. No.: WO95/02594
  PCT Pub. Date: Jan. 26, 1995

Related U.S. Application Data

[63] Continuation of Ser. No. 193,316, Feb. 8, 1994, abandoned, which is a continuation-in-part of Ser. No. 92,181, Jul. 15, 1993, abandoned.

[51] Int. Cl.$^6$ ............................................. A61K 31/70
[52] U.S. Cl. ............................................. 514/30; 536/7.1
[58] Field of Search ............................... 514/30; 536/7.1

[56] References Cited

U.S. PATENT DOCUMENTS

| | | | |
|---|---|---|---|
| 3,975,372 | 8/1976 | Ganguly et al. | 536/17 |
| 4,056,616 | 11/1977 | Reimann et al. | 424/180 |
| 4,279,896 | 7/1981 | Ganguly et al. | 514/30 |
| 4,490,524 | 12/1984 | Fujiwara et al. | 536/7.1 |
| 4,515,941 | 5/1985 | Fujiwara et al. | 536/7.1 |
| 4,579,940 | 4/1986 | Fujiwara et al. | 536/7.1 |
| 4,604,380 | 8/1986 | DeBono | 514/30 |
| 4,629,786 | 12/1986 | DeBono et al. | 536/7.1 |
| 4,804,749 | 2/1989 | Fijiwara et al. | 536/7.1 |
| 4,920,103 | 4/1990 | Kirst et al. | 514/30 |
| 4,921,947 | 5/1990 | Tao et al. | 536/7.1 |
| 4,945,081 | 7/1990 | Umezawa et al. | 514/30 |
| 4,962,146 | 10/1990 | Mallams et al. | 514/30 |
| 5,026,832 | 6/1991 | Fujiwara et al. | 536/7.1 |
| 5,032,581 | 7/1991 | Lukacs et al. | 514/30 |
| 5,043,324 | 8/1991 | Lukacs et al. | 514/30 |
| 5,101,022 | 3/1992 | Umezawa et al. | 536/7.1 |
| 5,140,014 | 8/1992 | Maring et al. | 514/30 |
| 5,545,624 | 8/1996 | Hecker et al. | 514/30 |

FOREIGN PATENT DOCUMENTS

| | | | |
|---|---|---|---|
| 0052005 | 5/1982 | European Pat. Off. | |
| 0394135 | 10/1990 | France | |
| 5117292 | 5/1993 | Japan | |
| 2135670 | 9/1984 | United Kingdom | C07H 17/08 |

OTHER PUBLICATIONS

B. S. Bal et al., Tetrahedron, vol. 37, pp. 2091–2096, 1981.
K. Funaishi et al., J. of Antibiotics, pp. 938–947, vol. XLIII No. 8, 1990.
H. Koshiyama et al., J. of Antibiotics, pp. 61–64, vol. XXII No. 2, 1969.
H. Kirst et al., J. of Antibiotics, pp. 1675–1682, vol. XXXV No. 12, 1982.
H. Kirst et al., J. of Antibiotics, pp. 823–842, vol. XL No. 6, 1987.
Wagman et al., J. of Antibiotics, pp. 641–646, vol. XXV No. 11, 1972.

*Primary Examiner*—John Kight
*Assistant Examiner*—Howard C. Lee
*Attorney, Agent, or Firm*—Peter C. Richardson; Gregg C. Benson

[57] ABSTRACT

The present invention relates to amide derivatives of formula (I) or (II) of 19-carboxy-19-deformyl 16-membered ring macrolide antibiotics rosaramicin, repromicin, tylosin, 5-O-mycaminosyltylonolide, 4-deoxy-O-mycaminosyltylonolide, desmycosin lactenocin, O-demethyllactenocin, cirramycin $A_1$, and 23-deoxymycaminosyltylonolide, which are useful against bacterial and mycoplasmic pathogens in animals. Also claimed are a pharmaceutical composition of such derivatives and their use in treating bacterial and mycoplasmic infections in animals.

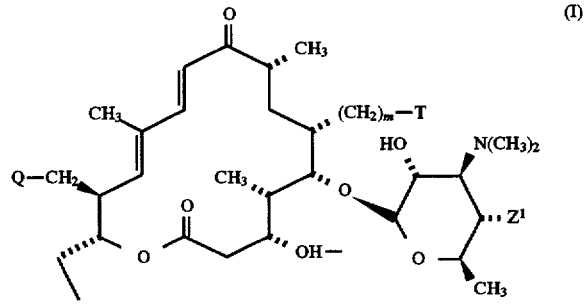

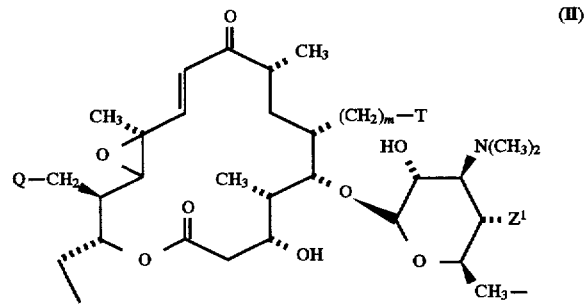

15 Claims, No Drawings

AMIDE DERIVATIVES OF 16-MEMBERED RING ANTIBIOTIC MACROLIDES

CROSS REFERENCE TO RELATED APPLICATIONS

This application is the national stage of PCT application number PCT/IB94/00199 having an international filing date of Jul. 4, 1994, which is a continuation of U.S. application Ser. No. 08/193,316, filed Feb. 8, 1994, now abandoned, which is a continuation-in-part of U.S. application Ser. No. 08/092,181, filed Jul. 15, 1993, now abandoned.

TECHNICAL FIELD

This invention is concerned with new antibiotics. In particular, this invention relates to compounds which are amide derivatives of the macrolide antibiotics rosaramicin, repromicin, tylosin, 5-O-mycaminosyltylonolide, 4'-deoxy-5-O-mycaminosyltylonolide, desmycosin, lactenocin, O-demethyllactenocin, cirramycin $A_1$, and 23-deoxymycaminosyltylonolide; to the pharmaceutically-acceptable acid addition salts of such derivatives; to a method of using such derivatives in the treatment of illnesses in animals caused by bacterial and mycoplasmic pathogens; and to pharmaceutical compositions useful therefor. The term "animals" includes mammals, fish and birds.

There are numerous agents known to combat bacterial infectious diseases in animals, but for many specific diseases the current agents of choice leave much to be desired. In some instances the agents may not persist long enough in the host and, therefore, require frequent dosing to maintain therapeutically effective blood and/or tissue levels. For meat producing animals (cattle, poultry, sheep and swine) this will require considerable labor intensive animal handling which is costly to the producer. In other cases, the agent may be poorly tolerated or even toxic to the host at therapeutically effective doses. Agents with increased potency, a longer half-life, an increased therapeutic index and a broader spectrum of antibacterial activity as well as agents with greater oral absorption would improve the scope of animal diseases that could be more effectively treated. Thus, the need for new antibacterial and anti-mycoplasmic agents with improved properties endures.

Diseases of particular concern are: bovine respiratory disease, the principal causative bacterial pathogens of which are *Pasteurella haemolytica*, *P. multocida* and *Haemophilus somnus*; pasteurellosis in swine, goats, sheep and poultry *P. multocida*); swine pleuropneumonia (*Actinobacillus pleuropneumoniae*); swine streptococcus infections (*Streptococcus suis*); and for all of the above mentioned hosts, infections by *Mycoplasma* spp.

BACKGROUND ART

Derivatives of tylosin and its related macrolides have been shown to be effective against infections in poultry, cattle and pigs caused by certain gram-positive and gram-negative bacteria: Kirst et al., U.S. Pat. No. 4,920,103; Tao et al., U.S. Pat. No. 4,921,947; Kirst et al., U.K. Patent Application GB 2135670A.

C-20 reductive amination products of the above macrolides are disclosed in U.S. patent application Ser. No. 07/914,242, filed Jul. 15, 1992 now abandoned in favor of co-pending U.S. patent application Ser. No. 07/996,243, filed Dec. 23, 1993 and assigned to the assignee hereof. C-20 Wittig reaction products of the above macrolides are disclosed in co-pending U.S. patent application Ser. No. 08/032,901, filed Mar. 18, 1993 and in co-pending U.S. patent application Ser. No. 08/145,456, filed Oct. 29, 1993, which is a continuation-in-part of U.S. patent application Ser. No. 08/032,901, both of which are assigned to the assignee hereof.

DISCLOSURE OF THE INVENTION

This invention is concerned with new antibiotics which are amide derivatives of the macrolides repromicin, rosaramicin, tylosin, 5-O-mycaminosyltylonolide, 4'-deoxy-5-O-mycaminosyltylonolide, desmycosin, lactenocin, O-demethyllactenocin, cirramycin $A_1$, and 23-deoxymycaminosyltylonolide and to the acid addition salts of such derivatives. These new antibiotics have enhanced potency against bacterial pathogens over the parent compounds and are active against mycoplasmic pathogens.

The compounds of the present invention and their pharmaceutically-acceptable salts are of the formula I or II

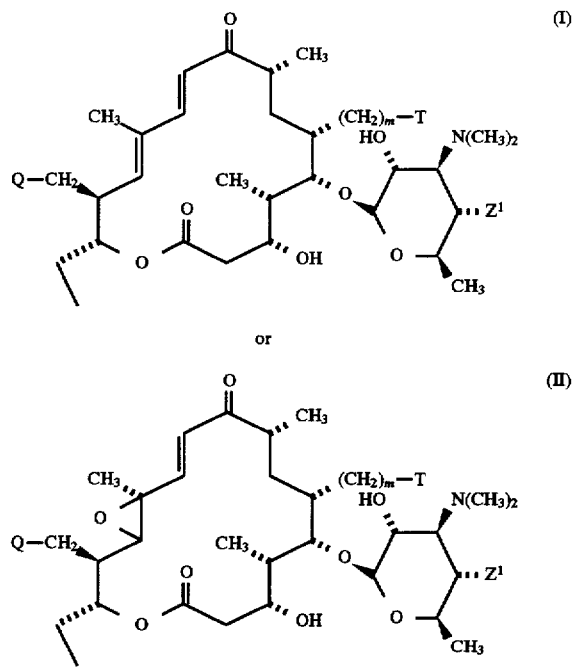

and the pharmaceutically acceptable salts thereof wherein
m is 1 or 2;
$Z^1$ is H, OH or mycarosyloxy;

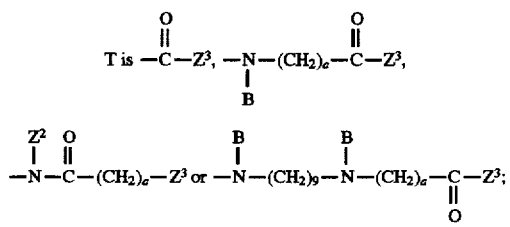

wherein
a is 1 or 2;
g is 2, 3, or 4;
B for each occurrence is independently selected from the group consisting of hydrogen, $(C_1-C_4)$alkyl, an aminoacyl group and a dipeptidyl group;
wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

$Z^2$ is hydrogen or $(C_1-C_4)$alkyl; and $Z^3$ is $-N(R^1R^2)$.

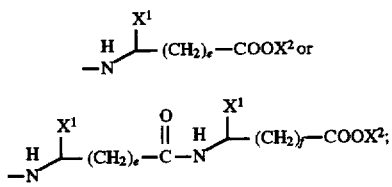

$R^1$ and $R^2$ are each independently selected from the group consisting of hydrogen, methyl, optionally substituted alkyl having 2 to 6 carbons, optionally substituted cycloalkyl having 3 to 8 carbons, aminoalkyl having 2 to 6 carbons, hydroxyalkyl having 2 to 6 carbons, N-alkylaminoalkyl having 1 to 4 carbons in the alkylamino portion and 2 to 4 carbons in the alkyl portion, benzyl, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion, morpholino-$(C_2-C_4)$alkyl, piperidino-$(C_2-C_4)$alkyl, pyrrolidino-$(C_2-C_4)$alkyl, azetidin-1-yl-$(C_2-C_4)$alkyl, and hexahydroazepin-1-yl-$(C_2-C_4)$alkyl;

wherein the optionally substituted alkyl is optionally substituted with 1 or 2 substituents independently selected from the group consisting of hydroxy, cyano, fluoro, trifluoromethyl, optionally substituted amino, optionally substituted N-alkylamino having 1 to 4 carbons, N,N-dialkylamino having a total of 2 to 6 carbons, N-(hydroxyalkyl)amino having 2 to 4 carbons, N,N-bis(hydroxyalkyl)amino wherein each alkyl portion has 2 to 4 carbons, alkoxy having 1 to 4 carbons, alkoxycarbonyl having 1 to 4 carbons in the alkoxy portion, N,N-dialkylaminoalkoxy having a total of 2 to 6 carbons in the dialkylamino portion and 2 to 4 carbons in the alkoxy portion, alkoxyalkoxy having 1 to 4 carbons in each of the alkoxy portions, alkoxyalkoxyalkoxy having 1 to 4 carbons in each of the alkoxy portions,

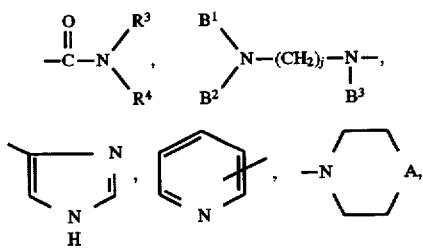

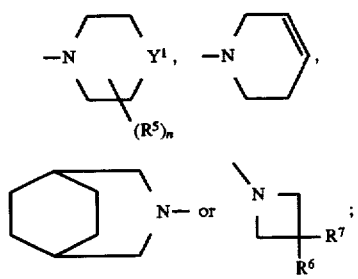

wherein the optionally substituted amino and the optionally substituted N-alkylamino are each independently optionally substituted with an aminoacyl group or a dipeptidyl group;

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

j is 2, 3, or 4;

$R^3$ and $R^4$ are independently selected from hydrogen and alkyl having 1 to 4 carbons;

or $R^3$ and $R^4$ are taken together with the nitrogen to which they are attached and form a saturated or unsaturated ring having 4 to 6 carbon atoms, morpholino or piperazino;

A is NH, S, N-$(C_1-C_4)$alkyl, N-(aminoacyl group), or N-(dipeptidyl group);

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

$B^1$, $B^2$, and $B^3$ are each independently selected from the group consisting of hydrogen, $(C_1-C_4)$alkyl, an aminoacyl group and a dipeptidyl group;

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

$Y^1$ is selected from the group consisting of C, CH, CH$_2$, N and NH;

n is 0, 1 or 2;

$R^5$ is alkyl having 1 to 4 carbons or

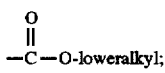

$R^6$ is alkyl having 1 to 4 carbons;

$R^7$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^6$ and $R^7$ are taken together and form an oxo group; the optionally substituted cycloalkyl is optionally substituted with 1 to 5 substituents independently selected from the group consisting of hydroxy, fluoro, chloro, alkoxy having 1 to 4 carbons, hydroxyalkyl having 1 to 4 carbons, alkoxyalkyl having 1 to 4 carbons in each of the alkoxy and alkyl portions, amino, N-alkylamino having 1 to 4 carbons and N,N-dialkylamino having a total of 2 to 6 carbons;

or $R^1$ and $R^2$ are taken together with the nitrogen to which they are attached and form

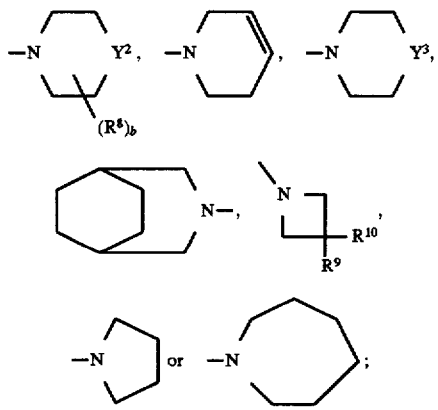

wherein $Y^2$ is selected from the group consisting of C, CH, CH$_2$, N, NH, N(aminoacyl group) and N(dipeptidyl group);

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N, N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

$Y^3$ is O or S;

b is 0, 1 or 2;

$R^8$ is alkyl having 1 to 4 carbons or

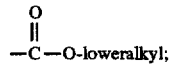

$R^9$ is H or alkyl having 1 to 4 carbons; and $R^{10}$ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or $R^9$ and $R^{10}$ are taken together and form an oxo group; and $X^1$ corresponds to just the side chain portion of amino acids and for each occurrence is independently selected from the side chain of the group of amino acids consisting of the D- or L- form, when applicable, of alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophan, tyrosine, valine, β-alanine, β-lysine, α,α-dimethylglycine, α-aminobutyric acid, 4-hydroxyphenylglycine, phenylglycine, α,γ-diaminobutyric acid, ornithine and homoserine;

e is 0 or 1, provided that when e is 1 then $X^1$ corresponds to the side chain of β-lysine or β-alanine;

f is 0 or 1, provided that when f is 1 then $X^1$ corresponds to the side chain of β-lysine or β-alanine;

$X^2$ is H, alkyl having 1 to 4 carbons or benzyl;

Q is selected from the group consisting of H, OH, fluoro, chloro, bromo, iodo, $OX^3$,

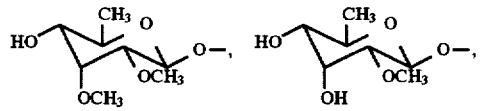

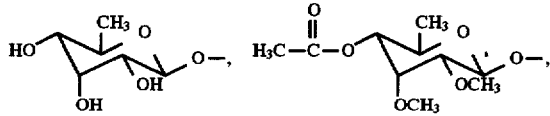

azetidin-1-yl, pyrrolidin-1-yl, piperidin-1-yl, 3,3-dimethylpiperidin-1-yl, hexahydroazepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino, 2,6-dimethylmorpholin-4-yl, thiomorpholino, and

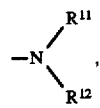

wherein $R^{11}$ and $R^{12}$ are independently selected from the group consisting of H, alkyl having 1 to 4 carbons, hydroxyalkyl having 2 to 4 carbons, cycloalkyl having 3 to 8 carbons, alkenyl having 3 or 4 carbons, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion; and $X^3$ is selected from the group consisting of optionally substituted alkyl having 1 to 4 carbons, optionally substituted cycloalkyl having 4 to 8 carbon atoms, and an optionally substituted aryl, aralkyl or heteroaryl group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl; wherein the optionally substituted alkyl and optionally substituted cycloalkyl can be substituted with 1 or 2 substituents independently selected from the group consisting of hydroxy, amino, N-alkylamino having 1 to 4 carbons, N,N-dialkylamino having a total of 2 to 6 carbons and alkoxy having 1 to 4 carbons; and where the optionally substituted aryl, aralkyl and heteroaryl groups are optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

provided that when $R^1$ or $R^2$ is a substituted alkyl or substituted cycloalkyl, then the hydroxy, alkoxy, fluoro, chloro, N-alkylamino, N,N-dialkylamino and amino substituents cannot be attached to the 1-position of said substituted alkyl or substituted cycloalkyl.

The term "loweralkyl" denotes an alkyl having 1 to 4 carbons. The term "alkyl" is meant to encompass both straight chain and branched alkyls.

Those skilled in the art will recognize that some of the compounds of the present invention possess new stereochemical centers. In those cases where new stereochemical centers are present it is understood that all of the stereoisomers are within the scope of this invention.

As will be readily apparent to one skilled in the art, when $X^3$ is an optionally substituted heteroaryl group, the oxygen, to which $X^3$ is attached, cannot be attached to the heteroaryl group through a heteroatom of the ring.

The aminoacyl groups are derivatives of the corresponding amino acids and are well known in the art. The following D- or L- amino acids, where applicable, are used to derive the aminoacyl groups of this invention: alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophane, tyrosine, valine, β-alanine, β-lysine, N,N-dimethylglycine, α,α-diaminobutyric α-aminobutyric acid, 4-hydroxyphenylglycine, phenylglycine, α,α-diaminobutyric acid, ornithine, homoserine, bicine, N,N-diethyl-β-alanine, N,N-dimethyl-γ-aminobutyric acid, and sarcosine. Those skilled in the art will recognize that certain of the above-named amino acids exist as both the D- and L-stereoisomer. The phrase used in the claim: "the D- or L- form, when applicable,", means that those skilled in the art will be apprised of which of the above-named amino acids can be in the D- or L-form. The present invention, therefore, encompasses both stereoisomers of those amino acids which exist in the D- and L- configuration.

The dipeptidyl groups comprise derivatives of any possible combination of two of the amino acids listed hereinabove which can be coupled by conventional peptide synthesis methods well known to those skilled in the art. Provided that N,N-dimethylglycine, bicine, N,N-diethyl-β-alanine or N,N-dimethyl-γ-aminobutyric acid can only be the terminal aminoacyl when in a dipeptidyl group.

A preferred group of compounds is the group having the formula (I) or (II) wherein m is 1; $Z^1$ is H and Q is H or OH.

Another preferred group of compounds is the group having the formula (I) wherein m is 1; $Z^1$ is H and Q is H.

A more preferred group of compounds is the group having the formula (I) wherein m is 1; $Z^1$ is H; Q is H; T is

wherein $Z^3$ is —$N(R^1R^2)$, wherein $R^1$ and $R^2$ are as defined above for formula (I).

An even more group of preferred compounds is the group having the formula (I) wherein m is 1; $Z^1$ is H; Q is H; T is

wherein $Z^3$ is —$N(R^1R^2)$ wherein $R^1$ is H, methyl or optionally substituted alkyl having 2 to 6 carbons; $R^2$ is aminoalkyl having 2 to 6 carbons, N-alkylaminoalkyl having 1 to 4 carbons in the alkylamino portion and 2 to 4 carbons in the alkyl portion, N, N-dialkylaminoalkyl having a total of 2 to 6 carbons in the dialkylamino portion and 2 to 4 carbons in the alkyl portion or optionally substituted alkyl having 2 to 6 carbons;

wherein the optionally substituted alkyl is optionally substituted with

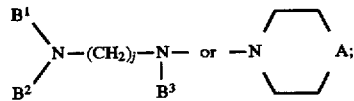

or $R^1$ and $R^2$ are taken together with the nitrogen to which they are attached and form

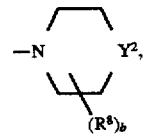

wherein $B^1$, $B^2$, $B^3$, j, A, $Y^2$, $R^8$ and b are as defined above for formula (I). A more preferred group of compounds within the immediately above group of preferred compounds is the group wherein $R^1$ and $R^2$ are taken together with the nitrogen to which they are attached and form

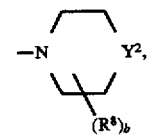

wherein b is 0 and $Y^2$ is NH or b is 1 and $Y^2$ is N, NH, CH or $CH_2$.

Another preferred group of compounds is the group having the formula (I) wherein m is 2; $Z^1$ is H; Q is H; T is

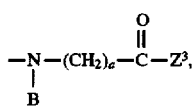

wherein B, a and $Z^3$ are as defined above for formula (I).

Another more preferred group of compounds is the group having the formula (I) wherein m is 2; $Z^1$ is H; Q is H; T is

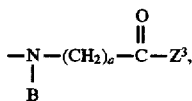

wherein B is H or methyl; a is as defined above for formula (I) and $Z^3$ is —$N(R^1R^2)$, wherein $R^1$ and $R^2$ are as defined above for formula (I).

A most preferred group of compounds is the group having the formula (I) wherein m is 2; $Z^1$ is H; Q is H; T is

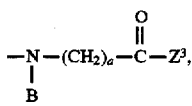

wherein B is H or methyl; a is 1; and $Z^3$ is —$N(R^1R^2)$ wherein $R^1$ is H, alkyl or aminoalkyl; and $R^2$ is aminoalkyl, N-alkylamino-alkyl having 1 to 4 carbons in the aminoalkyl portion and 2 to 4 carbons in the alkyl portion or N,N-dialkylaminoalkyl having a total of 2 to 6 carbons in the dialkylamino portion and 2 to 4 carbons in the alkyl portion; or $R^1$ and $R^2$ are taken together with the nitrogen to which they are attached and is piperazinyl.

The compounds of the present invention, having the formula I or II, as defined above, are according to this invention readily and generally prepared by conversion of the appropriate macrolide, rosaramicin, repromicin, tylosin, 5-O-mycaminosyltylonolide, 4'-deoxy-5-O-mycaminosyltylonolide, desmycosin, lactenocin, O-demethyllactenosin, cirramycin $A_1$, or 23-deoxymycaminosyltylonolide to the derived carboxylic acid followed by reaction with an amine, and optionally followed by conversion to the acid addition salt as detailed below.

Derivatization of the parent macrolide at the C-23 position is carried out according to the method well known to those skilled in the art and as described in J. Antibiotics, 40(6), pp. 823–842, 1987, the contents of which are incorporated herein by reference.

The starting macrolide rosaramicin is produced and isolated according to the method described by Wagman et al. in Journal of Antibiotics, Vol. XXV, No. 11, pp. 641–646, November 1972. Repromicin is synthesized from rosaramicin using the method taught by Ganguly et al. in U.S. Pat. No. 3,975,372. Desmycosin, lactenocin, O-demethyllactenocin and 23-deoxymycaminosyltylonolide are produced and isolated according to the method described in Journal of Antibiotics, 35(12), pp. 1675–1682, 1982. Cirramycin $A_1$, is produced and isolated according to the method described in Journal of Antibiotics, 22, p. 61, 1969. The contents of the above references are incorporated herein by reference. All other starting materials and reagents required for the synthesis of the compounds of the present invention are readily available commercially or can be prepared according methods known in the literature.

The compounds of this invention wherein T is

are synthesized according to the following procedure. The C-20 aldehyde of a series of tylosin-type macrolides is oxidized to the carboxylic acid. The intermediate carboxylic acid derivative of the macrolides are then coupled with a variety of amines to form amide derivatives. For example, repromicin, suitably protected as the 2'-acetate, is treated with approximately 1.3 equivalents of sodium chlorite in the presence of approximately 1.3 equivalents of sodium phosphate monobasic and an excess of 2-methyl-2-butene, about 7.0 equivalents. This oxidation step is usually carried out at ambient room temperature (20°–25° C.) using a 3:1 mixture of acetone/butanol as the solvent (0.3 to 0.5 molar concentration). In order to form the amide derivatives, the carboxylic acid is coupled with primary or secondary amines in the presence of about 1.1 equivalents of diethyl cyanophosphate and about 1.1 equivalents of triethylamine at about 0° C. using anhydrous DMF as the solvent (0.1 molar concentration). The reaction is worked up by pouring it into saturated aqueous $NaHCO_3$ and extracting with EtOAc. The isolated product is purified by flash chromatography (89% $CHCl_3$, 10% MeOH, 1% $Et_3N$) to afford the C-20 amide derivative. The 2'-acetate group can be removed by dissolving the above product in methanol (MeOH). The resulting solution is then stirred at room temperature (20°–25° C.) for about 18–24 hours. The reaction mixture is concentrated under reduced pressure to afford the C-20 amide derivative of repromicin.

Alternatively, compounds of this invention wherein T is

are synthesized from the C-20 carboxylic acid of the 2'-acetate of the tylosin-type macrolides according to the following method. To a 0.1M solution of the C-20 carboxylic acid in a polar aprotic solvent such as $CH_2Cl_2$, which has been cooled to about 0° C., is added about 5 equivalents of either a primary or a secondary amine. Propylphosphonic anhydride (1.4 equivalents) is added as a 50% solution in $CH_2Cl_2$ and the reaction is allowed to warm to ambient temperature. After stirring for about 1–5 hours the reaction mixture is concentrated in vacuo and then redissolved in MeOH to cleave the 2'-acetate. The reaction mixture is concentrated after stirring overnight and extracted from a basic aqueous solution to provide the C-20 repromicin amide.

The compounds of this invention wherein T is

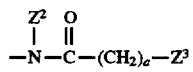

are readily prepared by the following method. The desired macrolide is reductively aminated with an amine in the presence of sodium triacetoxyborohydride as described hereinabove. The resulting aminated macrolide is then coupled with the desired carboxylic acid according to one of the coupling methods described hereinabove.

The amino amide compounds of this invention wherein T is

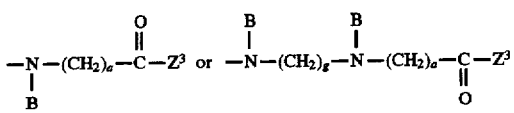

can be synthesized by the following two general methods. Certain amino amide fragments are available commercially or can be prepared from an amino acid such as glycine, sarcosine or β-alanine and a variety of amines by the same methods described hereinabove for the carboxylic acid derivatives of the macrolides described in this invention. The amine moiety of the amino acid portion can then be coupled with the C-20 macrolide aldehyde by reductive amination methods known to those skilled in the art. The following method can be employed. The desired macrolide, an amine, usually about 1.5 equivalents, and acetic acid are stirred in a reaction-inert solvent such as methylene chloride for about 30 to 60 minutes. After cooling to about 0° C., powdered sodium sulfate (about 10 equivalents) and sodium triacetoxyborohydride, about 1.1 equivalents, are added and the reaction solution is stirred at ambient temperature for about 1 to 12 hours. The desired C-20 amino macrolide derivative is then isolated by standard techniques well known to those Skilled in the art, such as column chromatography or crystallization. Alternatively, the reductive amination can first be performed with the C-20 aldehyde and a protected amino acid. Following deprotection, the acid can then be coupled to a variety of amines by the methods described hereinabove.

The pharmaceutically acceptable acid addition salts of the C-20 amide macrolide derivatives can be obtained by the following general procedure. For example, the HCl salts can be isolated by dissolving the C-20 amide macrolide derivative in a methanolic HCl solution and then evaporating the volatile components to yield the desired salt. The methanolic HCl solution can be prepared by mixing acetyl chloride with methanol. In addition to the HCl salts, other preferred pharmaceutically acceptable acid addition salts include citrate, phosphate, sulfate, methanesulfonate, benzenesulfonate, palmitate, succinate, lactate, malate, tartrate, fumerate and stearate salts. All of such salts are prepared in a method analogous to the method used to form the HCl salt.

The antibacterial activity of the compounds of the present invention against bacterial pathogens is demonstrated by the compound's ability to inhibit growth of *Pasteurella multocida* and *Pasteurella haemolytica*. The following procedures are typical assays. Assay I is utilized to test for activity against *Pasteurella multocida* and Assay II is utilized to test for activity against *Pasteurella haemolytica*.

Assay I (*P. multocida*)

This assay is based on the liquid dilution method in microliter format. A single colony of *P. multocida* (strain 59A067) is inoculated into 5 mL of brain heart infusion (BHI) broth. The test compounds are prepared by solubilizing 1 mg of the compound in 125 µl of dimethylsulfoxide (DMSO). Dilutions of the test compound are prepared using uninoculated BHI broth. The concentrations of the test compound used range from 200 µg/mL to 0.098 µg/mL by two-fold serial dilutions. The *P. multocida* inoculated BHI is diluted with uninoculated BHI broth to make a $10^4$ cell suspension per 200 µl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay II (*P. haemolytica*)

This assay is based on the agar dilution method using a Steers Replicator. Two to five colonies isolated from an agar plate are inoculated into BHI broth and incubated overnight at 37° C. with shaking (200 rpm). The next morning, 300 µl of the fully grown *P. haemolytica* preculture is inoculated into 3 mL of fresh BHI broth and is incubated at 37° C. with shaking (200 rpm). The appropriate amounts of the test compounds are dissolved in ethanol and a series of two-fold serial dilutions are prepared. Two mL of the respective serial dilution is mixed with 18 mL of molten BHI agar and solidified. When the inoculated *P. haemolytica* culture reaches 0.5 McFarland standard density, about 5 µl of the *P. haemolytica* culture is inoculated onto BHI agar plates containing the various concentrations of the test compound using a Steers Replicator and incubated for 18 hours at 37° C. Initial concentrations of the test compound range from 100–200 µg/mL. The MIC is equal to the concentration of the test compound exhibiting 100% inhibition of growth of *P. haemolytica* as determined by comparison with an uninoculated control.

The in vivo activity of the compounds of formula I or II can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 mL of a $3\times10^3$ CFU/mL bacterial suspension (*P. multocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or per os. Subcutaneous doses are administered into the loose skin in the back of the neck whereas oral doses are given by means of a feeding needle. In both cases, a volume of 0.2 mL is used per mouse. Compounds are administered 30 minutes, 4 hours, and 24 hours after challenge. A control compound of known efficacy administered by the same route is included in each test. Animals are observed daily, and the number of survivors in each group is recorded on the form provided. The *P. multocida* model monitoring continues for 96 hours (four days) post challenge. Surviving mice are asphyxiated with carbon dioxide at the end of the study.

The $PD_{50}$ is a calculated dose at which the compound tested protects 50% of a group of mice from mortality due to the bacterial infection which would be lethal in the absence of drug treatment.

To implement the methods of this invention, an effective dose of a compound of formula I or II is administered to a susceptible or infected animal by parenteral (i.v., i.m. or s.c.), oral or topical route. The effective dose will vary with the severity of the disease, and the age, weight and condition of the animal. However, the dose will usually range from about 0.25 to about 150 mg/kg per day, preferably from about 0.25 to about 25 mg/kg per day.

A suitable vehicle for administering the dose parenterally is a solution of the compound in sterile water, or a solution of the compound in a solvent comprising at least 50% water and a pharmaceutically acceptable cosolvent or cosolvents such as methanol, ethanol, isopropyl alcohol, propylene glycol, glycerol, carbonate esters like diethyl carbonate, dimethyl sulfoxide, N,N-dimethylformamide, N,N-dimethylacetamide, 1-methyl-2-pyrrolidinone, and the like. Suspensions are also suitable vehicles for administering the compounds of this invention. The suspending medium can be, for example, aqueous carboxymethyl cellulose, inert oils such as peanut oil, highly refined mineral oils, aqueous polyvinylpyrrolidone and so forth. Suitable physiologically acceptable adjuvants may be necessary to maintain the compound in suspension. These adjuvants may be chosen from among thickeners such as carboxymethyl cellulose, polyvinylpyrrolidone, gelatin, and the alginates. Surfactants are also useful as suspending agents. These suffactants include: lethicin, alkylphenol polyethylene oxide adducts, naphthalenesulfonates, alkylbenzenesulfonates and polyoxyethylene sorbitan esters. Agents affecting surface tension can also help in making useful suspensions. Such agents include silicone antifoams, sorbitol, and sugars. For intravenous use the total concentration of solutes should be controlled to render the preparation isotonic.

Thus, in a further aspect, the invention provides pharmaceutical compositions comprising a compound of the formula (I) or (II) or a pharmaceutically acceptable salt thereof together with a pharmaceutically acceptable carrier or diluent.

This invention also provides a method of treating a bacterial infection or a mycoplasmic infection in an animal in need thereof which method comprises administering to said animal a bacterial or mycoplasmic treating amount of a compound of the formula (I) or (II) or a pharmaceutically acceptable salt thereof.

The present invention is illustrated by the following examples, but is not limited to the details thereof. High Performance Liquid Chromatography (HPLC) retention times of the products of this invention are determined on a YMC 5 micron C-8 column (4.6 mm ID×250 mm length) from Eicon Scientific (P.O. Box 70, Medway, Mass. 508-533-7697). A 35:65 (vol:vol) mixture of acetonitrile to aqueous 50 millimolar ammonium acetate is used as the eluent. The column temperature is maintained at room temperature and the flow rate is 1.0 mL per minute. Samples are dissolved in the pre-mixed eluent (1 mg/mL) and are injected (20 μl) into a LDC CM 4000 pump and detected with an LDC SM 3100 detector. Peaks corresponding to the sample input are detected by ultraviolet spectroscopy at either 254 or 280 nm.

EXAMPLE 1

Method A

20-Oxo-20-[3-(dimethylamino)propylamino] repromicin

A solution containing 7.60 g of repromicin-2'-acetate (prepared according to the procedure described in U.S. Pat. No. 4,056,616) and 9.30 mL of 2-methyl-2-butene in 30 mL of acetone and 10 mL of butanol was stirred at room temperature. A solution containing 1.50 g of sodium chlorite and 2.25 g of sodium phosphate monobasic in 10 mL of $H_2O$ was added dropwise to the reaction mixture at room temperature. The resulting reaction mixture was stirred at room temperature for about 5 hours. It was then poured into 40 mL of saturated aqueous $Na_2SO_4$ and extracted with 4×40 mL of ethyl acetate (EtOAc). The combined organic layers were washed with 50 mL of brine, dried ($Na_2SO_4$), and concentrated under reduced pressure to give 7.25 g of the C-20 carboxylic acid. The carboxylic acid, 700 mg, was dissolved in 10 mL of anhydrous DMF along with 140 μl of 3-dimethylaminopropylamine. The resulting reaction mixture was cooled to about 0° C. Diethyl cyanophosphate (187 μl) was added at about 0° C., followed by 170 μl of triethylamine. The reaction mixture was stirred at about 0° C. for about 45 min. It was then poured into 30 mL of saturated aqueous $NaHCO_3$ and extracted with 4×40 mL of EtOAc. The combined organic layers were washed with 50 mL of brine, dried ($Na_2SO_4$), and concentrated under reduced pressure to give 650 mg of the crude amide. This crude amide was dissolved in 10 mL of MeOH and the resulting solution was stirred at room temperature overnight to remove the 2'-acetate group. The following morning, the reaction mixture was concentrated under reduced pressure. The crude product was then purified by flash chromatography (89% $CH_2Cl_2$, 10% MeOH, 1% $Et_3N$) to give 340 mg of the title product. Mass spec.=667; HPLC Ret. time (min)=6.04.

EXAMPLE 2

20-Oxo-20-(piperazinyl)repromicin

The C-20 carboxylic acid of repromicin-2'-acetate was prepared according to the procedure outlined in Example 1. The C-20 carboxylic acid, 870 mg, was dissolved in 5 mL of anhydrous DMF along with 260 mg of t-butyl-1-piperazinyl carboxylate. The resulting solution was cooled to about 0° C. and 230 μl of diethyl cyanophosphate was added, followed by 210 μl of triethylamine. The resulting reaction mixture was stirred at about 0° C. for about 1 hour. It was then poured into 20 mL of saturated aqueous $NaHCO_3$ and extracted with chloroform. The combined organic layers were washed with brine, dried ($Na_2SO_4$), and concentrated to give the crude amide. This crude amide was dissolved in 20 mL of MeOH and the resulting solution was stirred at room temperature for about 48 hours to remove the 2'-acetate group. The reaction mixture was then concentrated and the resulting crude product was purified by flash chromatography (89% $CHCl_3$, 10% MeOH, 1% $Et_3N$) to give 643 mg of the BOC-protected amide. This material was then dissolved in 10 mL of $CH_2Cl_2$ along with 1 mL of anhydrous TFA and the resulting solution was stirred at room temperature for about 18 hours. The reaction mixture was concentrated and the residue was taken up in 20 mL of $H_2O$ and basified with 1N NaOH. The aqueous layer was extracted with $CHCl_3$. The combined organic layers were washed with brine, dried ($Na_2SO_4$), and concentrated to give 448 mg of the title compound. Mass spec.=651; HPLC Ret. time (min.)=6.50.

EXAMPLE 3

20-oxo-20-[1-(L-alanyl)-4-piperazinyl]repromicin

20-Oxo-20-(piperazinyl)repromicin (100 mg) was dissolved in 2 mL of anhydrous DMF along with 29 mg of N-BOC-L-alanine. The resulting reaction mixture was cooled to about 0° C. and diethyl cyanophosphate (26 μl) was added, followed by triethylamine (24 μl). The reaction mixture was stirred at about 0° C. for about 2 hours. It was then poured into 10 mL of saturated aqueous NaHCO₃ and extracted with CHCl₃. The combined organic layers were washed with brine, dried (Na₂SO₄), and concentrated. The crude product was purified by flash chromatography (89% CHCl₃, 10% MeOH, 1% Et₃N) to give the BOC-protected amide. This material was dissolved in 5 mL of CH₂Cl₂ along with 500 µl of anhydrous TFA and the resulting solution was stirred at room temperature for about 18 hours. The reaction mixture was concentrated and the residue was taken up in H₂O and basified with 1N NaOH to a pH of 10. The aqueous layer was extracted with CHCl₃. The combined organic layers were washed with brine, dried (Na₂SO₄), and concentrated to give 86 mg of the title product. Mass spec.=722.

EXAMPLE 4

20-Oxo-20-[3-(pyrrolidino)propylamino]-5-O-mycaminosyltylonolide

A solution containing 3.0 g of 5-O-mycaminosyltylonolide (OMT) and 1.70 mL of acetic anhydride in 20 mL of acetone was stirred at room temperature. Triethylamine (2.50 mL) was added and the resulting reaction mixture was stirred at room temperature for about 48 hours. It was then concentrated under reduced pressure and the residue was taken up in 150 mL of CHCl₃. The organic layer was washed with 30 mL of saturated aqueous NaHCO₃, 2×30 mL of brine, dried (Na₂SO₄), and concentrated to give 3.3 g of the 23, 2', 4'- triacetate derivative of OMT. The triacetate derivative of OMT, 2.0 g, was dissolved in 10 mL of acetone and 6 mL of t-butanol along with 2.0 mL of 2-methyl-2-butene. A solution containing 406 mg of sodium chlorite and 496 mg of sodium phosphate monobasic in 10 mL of H₂O was added dropwise at room temperature for about 3 hours. It was then poured into 40 mL of saturated aqueous Na₂SO₄ and extracted with CHCl₃. The combined organic layers were washed with brine, dried (Na₂SO₄), and concentrated to give 1.92 g of the C-20 carboxylic acid derivative of OMT-23,2',4'-triacetate.

The C-20 carboxylic acid of OMT, 500 mg, was dissolved in 3 mL of anhydrous DMF along with 87 mg of N-(3-aminopropyl)-pyrrolidine. The resulting solution was cooled to about 0° C. Diethyl cyanophosphate (110 µL) was added, followed by triethylamine (100 µL). The resulting reaction mixture was stirred at about 0° C. for about 1 hour. The reaction mixture was then poured into 20 mL of saturated aqueous NaHCO₃ and extracted with CHCl₃. The combined organic layers were washed with brine, dried (Na₂SO₄), and concentrated. The residue was redissolved in 10 mL of MeOH along with 470 µl of triethylamine. The reaction mixture was stirred at room temperature for about 18 hours and then concentrated under reduced pressure. Chromatography (89% CHCl₃, 10% MeOH, 1% Et₃N) afforded 126 mg of the title product. Mass spec.=725.

EXAMPLE 5

Method B

20-Oxo-20-(N-[2-(methylamino)ethyl]-N-methylamino)repromicin

To a 0.1M solution of 250 mg of the C-20 carboxylic acid of repromicin in CH₂Cl₂ at about 0° C. was added 213 µl ethylene diamine. Propylphosphonic anhydride (1.4 eq., 356 mg) was added as a 50% solution in CH₂Cl₂ and the reaction was allowed to warm to ambient temperature. After stirring for about 2.5 hours, the reaction mixture was concentrated to afford a yellow foam, and then redissolved in 5 mL MeOH and stirred overnight at ambient temperature to cleave the 2' acetate. The reaction solution was concentrated and the resulting yellow foam was dissolved in 5 mL H₂O and acidified to pH 4 with glacial acetic acid. The aqueous solution was washed with CH₂Cl₂ (2×25 mL), then basified to pH 5 with saturated aqueous NaHCO₃ and extracted again with CH₂Cl₂ (2×25 mL). The aqueous solution was then basified to pH 8 with more aqueous NaHCO₃ and extracted with CH₂Cl₂ (3×25 mL). This final CH₂Cl₂ solution was dried over Na₂SO₄, filtered and concentrated to afford 98 mg of the title product. Mass spec.=652; HPLC Ret. time (min.)=6.32.

EXAMPLE 6

Method C

20-[4-(2-Oxo-2-pyrrolidin-1-yl-ethyl)-piperazin-1-yl]-20-deoxorepromicin

To a solution of 1-(pyrrolidino carbonyl methyl) piperazine (209 mg, 1.06 mmol) and repromicin (200 mg, 0.35 mmol) in dichloromethane at about 0° C. was added glacial acetic acid (100 µL, 1.77 mmol) and sodium sulfate (500 mg, 3.5 mmol). After stirring for about one hour sodium triacetoxyborohydride (82 mg, 0.388 mmol) was added, the mixture was allowed to warm to room temperature and was stirred until the reaction was complete, about two hours. The mixture was filtered, washed with saturated aqueous sodium bicarbonate and brine, dried (Na₂SO₄), filtered and concentrated to a yellow foam. The crude product was purified by column chromatography on silica gel, eluting with 0.5% NH₄OH in 98:2 CH₂Cl₂/MeOH, to afford 154 mg (58%) of the desired product. Mass spec.= 747; HPLC RT=10.25 minutes.

EXAMPLES 7–26

Compounds of Examples 7–26 having the general formula

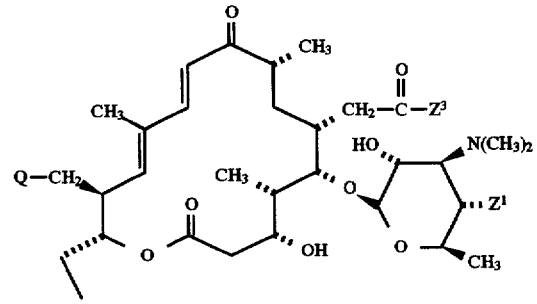

were prepared according to the method shown.

| Ex. No. | Z³=N(R¹R²) | Z¹ | Q | Prep. Meth. | Mass Spec. | HPLC RT (min) |
| --- | --- | --- | --- | --- | --- | --- |
| 7 | 1-methylpiperazinyl | H | H | A | 665 | 10.82 |
| 8 | N-[3-(dimethylamino) propyl)-N-3-(dimethyl- amino)propylamino | H | H | A | 752 | 9.30 |
| 9 | N-[3-(dimethylamino) propyl]-N-methylamino | H | H | A | 681 | 6.99 |
| 10 | 2-(dimethylamino)ethyl- amino | H | H | A | 653 | 6.43 |
| 11 | 3-(morpholino)propylamino | H | H | A | 709 | 9.11 |

17
-continued

| Ex. No. | $Z^3$=N(R$^1$R$^2$) | $Z^1$ | Q | Prep. Meth. | Mass Spec. | HPLC RT (min) |
|---|---|---|---|---|---|---|
| 12 | histaminyl | H | H | A | 676 | 8.63 |
| 13 | 4-(dimethylamino)butyl-amino | H | H | A | 681 | 6.30 |
| 14 | 3-(N,N-bis-hydroxyethyl)-propylamino | H | H | A | 727 | 5.48 |
| 15 | 1-(glycyl)-4-piperazinyl | H | H | A | 936 | 2.65 |
| 16 | 1-(L-seryl)-4-piperazinyl | H | H | A | 966 | 5.75 |
| 17 | N-[3-(dimethylamino)propyl]-N-methylamino | OH | OH | A | 713 | 3.23 |
| 18 | 1-methylpiperazinyl | OH | OH | A | 697 | 3.57 |
| 19 | 3-aminopropylamino | H | H | B | 638 | 5.45 |
| 20 | N-[3-(methylamino)propyl]-N-methylamino | H | H | B | 666 | 6.32 |
| 21 | N-{2-[N-2-(methylamino)ethyl-N-methylamino]ethyl}-N-methylamino | H | H | B | 709 | 7.98 |
| 22 | L-alanylethyl ester | H | H | B | 681 | 28.97 |
| 23 | L-glycylethyl ester | H | H | B | 667 | 19.40 |
| 24 | glycylglycylethyl ester | H | H | B | 724 | 14.00 |
| 25 | glycylglycylbenzyl ester | H | H | B | 785 | 10.64 |
| 26 | N-[3-(4-methyl-piperazin-1-yl)-propyl]amino | H | H | B | 721 | 8.62 |

Mass Spectra were obtained by either last atom bombardment or electron impact methods.

EXAMPLES 27–28

Compounds of Examples 27 and 28 having the general formula

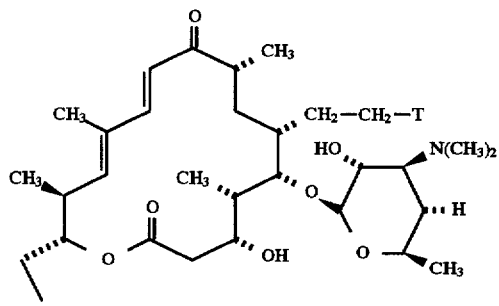

were synthesized according to the methods shown.

| Ex. No. | T | Prep. Method | *Mass Spectra | HPLC RT (min) |
|---|---|---|---|---|
| 27 | 4-(2-isopropylamino-2-oxo-ethyl)-piperazin-1-yl | C | 735 | 12.60 |
| 28 | 4-(2-morpholin-4-yl-2-oxo-ethyl)-piperazin-1-yl | C | 763 | 7.95 |

*Mass spectra were obtained by either fast atom bombardment or electron impact methods.

EXAMPLES 29–37

Compounds of Examples 29–37 having the general formula

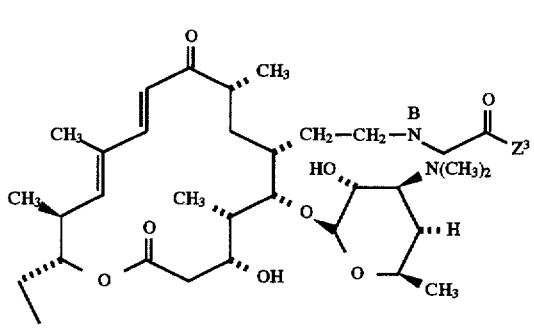

were synthesized according to the methods shown.

| Ex. No | $Z^3$ | B | [1]Prep. Method | *Mass Spectra | HPLC RT (min) |
|---|---|---|---|---|---|
| 29 | N-[2-(dimethylamino)ethyl]-N-methylamino | H | B,C | 709 | 8.34 |
| 30 | N-[3-(dimethylamino)propyl]-N-N-methylamino | H | B,C | 723 | 7.53 |
| 31 | 2-(dimethylamino)ethylamino | H | B,C | 695 | 6.51 |
| 32 | 3-(dimethylamino)propylamino | H | B,C | 709 | 7.68 |
| 33 | 2-(methylamino)ethylamino | Me | C,B | 695 | 7.14 |
| 34 | 2-aminoethylamino | Me | C,B | 681 | 6.09 |
| 35 | N-[2-(methylamino)ethyl]-N-methylamino | Me | C,B | 709 | 6.18 |
| 36 | N-[2-(dimethylamino)ethyl]-N-methylamino | Me | C,B | 723 | 8.60 |
| 37 | piperazinyl | Me | C,B | 707 | 6.53 |

*Mass spectra were obtained by either fast atom bombardment or electron impact methods.
[1]The first letter indicates the first reaction step method and the second letter indicates the second and final reaction step method.

We claim:
1. A compound of formula I or II

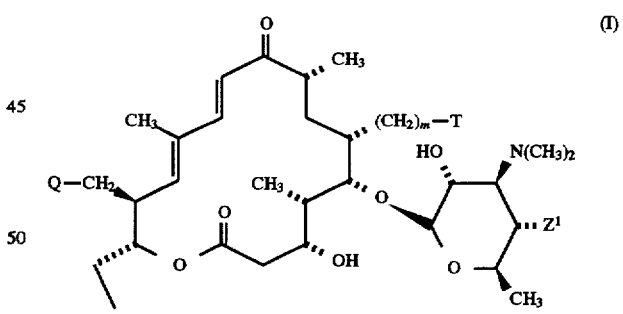

(I)

or

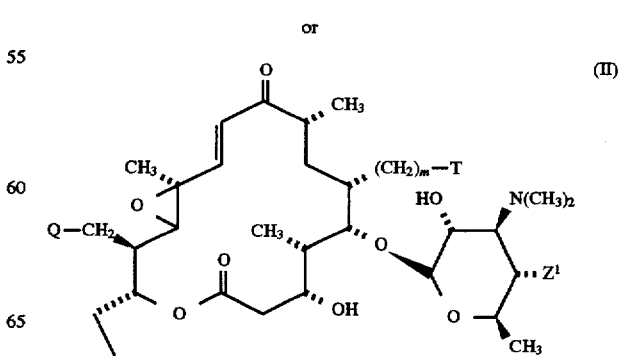

(II)

and the pharmaceutically acceptable salts thereof wherein m is 1 or 2;

$Z^1$ is H, OH or mycarosyloxy;

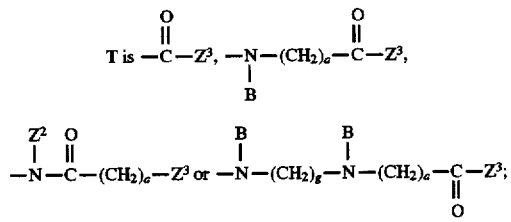

wherein a is 1 or 2;

g is 2, 3, or 4;

B for each occurrence is independently selected from the group consisting of hydrogen, $(C_1-C_4)$alkyl, an aminoacyl group and a dipeptidyl group;

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

$Z^2$ is hydrogen or $(C_1-C_4)$alkyl; and $Z^3$ is $-N(R^1R^2)$,

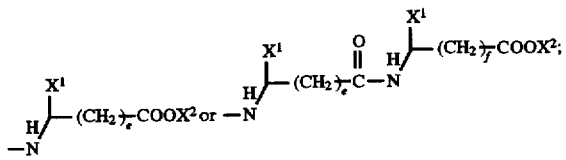

$R^1$ and $R^2$ are each independently selected from the group consisting of hydrogen, methyl, optionally substituted alkyl having 2 to 6 carbons, optionally substituted cycloalkyl having 3 to 8 carbons, aminoalkyl having 2 to 6 carbons, hydroxyalkyl having 2 to 6 carbons, N-alkylaminoalkyl having 1 to 4 carbons in the alkylamino portion and 2 to 4 carbons in the alkyl portion, benzyl, alkoxyalkyl having 2 to 4 carbons in the alkyl portion and 1 to 4 carbons in the alkoxy portion, N,N-dialkylaminoalkyl having a total of 2 to 6 carbons in the dialkylamino portion and 2 to 4 carbons in the alkyl portion, morpholino-$(C_2-C_4)$alkyl, piperidino-$(C_2-C_4)$alkyl, pyrrolidino-$(C_2-C_4)$alkyl, azetidin-1-yl-$(C_2-C_4)$alkyl, and hexahydroazepin-1-yl-$(C_2-C_4)$alkyl;

wherein the optionally substituted alkyl is optionally substituted with 1 or 2 substituents independently selected from the group consisting of hydroxy, cyano, fluoro, trifluoromethyl, optionally substituted amino, optionally substituted N-alkylamino having 1 to 4 carbons, N,N-dialkylamino having a total of 2 to 6 carbons, N-(hydroxyalkyl)amino having 2 to 4 carbons, N,N-bis(hydroxyalkyl)amino wherein each alkyl portion has 2 to 4 carbons, alkoxy having 1 to 4 carbons, alkoxycarbonyl having 1 to 4 carbons in the alkoxy portion, N,N-dialkylaminoalkoxy having a total of 2 to 6 carbons in the dialkylamino portion and 2 to 4 carbons in the alkoxy portion, alkoxyalkoxy having 1 to 4 carbons in each of the alkoxy portions, alkoxyalkoxyalkoxy having 1 to 4 carbons in each of the alkoxy portions,

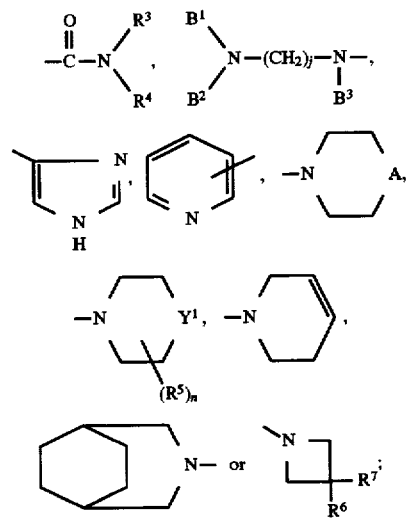

wherein the optionally substituted amino and the optionally substituted N-alkylamino are each independently optionally substituted with an aminoacyl group or a dipeptidyl group;

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N, N-dimethylglycyl, bicyl, N,N-diethyl-β-alanyl or N,N-dimethyl-γ-aminobutyryl can only be the terminal aminoacyl when in a dipeptidyl group;

j is 2, 3, or 4;

$R^3$ and $R^4$ are independently selected from hydrogen and alkyl having 1 to 4 carbons;

or $R^3$ and $R^4$ are taken together with the nitrogen to which they are attached and form a saturated or unsaturated ring having 4 to 6 carbon atoms, morpholino or piperazino;

A is NH, S, N-$(C_1-C_4)$alkyl, N-(aminoacyl group), or N-(dipeptidyl group);

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

B¹, B², and B³ are each independently selected from the group consisting of hydrogen, (C₁-C₄)alkyl, an aminoacyl group and a dipeptidyl group;

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

Y¹ is selected from the group consisting of C, CH, CH₂, N and NH;

n is 0, 1 or 2;

R⁵ is alkyl having 1 to 4 carbons or

loweralkyl;

R⁶ is alkyl having 1 to 4 carbons;

R⁷ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or R⁶ and R⁷ are taken together and form an oxo group;

the optionally substituted cycloalkyl is optionally substituted with 1 to 5 substituents independently selected from the group consisting of hydroxy, fluoro, chloro, alkoxy having 1 to 4 carbons, hydroxyalkyl having 1 to 4 carbons, alkoxyalkyl having 1 to 4 carbons in each of the alkoxy and alkyl portions, amino, N-alkylamino having 1 to 4 carbons and N,N-dialkylamino having a total of 2 to 6 carbons;

or R¹ and R² are taken together with the nitrogen to which they are attached and form

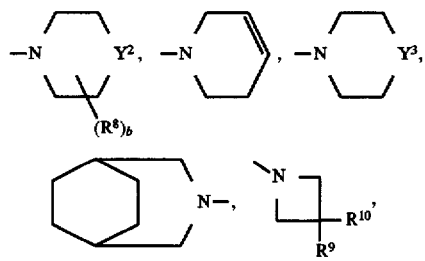

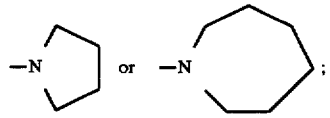

wherein Y² is selected from the group consisting of C, CH, CH₂, N, NH, N(aminoacyl group) and N(dipeptidyl group);

wherein the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxylysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl, provided that N,N-dimethylglycyl, bicyl, N,N-diethyl-β-alanyl or N,N-dimethyl-γ-aminobutyryl can only be the terminal aminoacyl when in a dipeptidyl group;

Y³ is O or S;

b is 0, 1 or 2;

R⁸ is alkyl having 1 to 4 carbons or

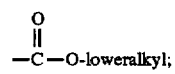

R⁹ is H or alkyl having 1 to 4 carbons; and

R¹⁰ is selected from the group consisting of H, alkyl having 1 to 4 carbons, hydroxy, alkoxy having 1 to 3 carbons, amino, N-alkylamino having 1 to 4 carbons and N,N-dialkylamino having a total of 2 to 6 carbons;

or R⁹ and R¹⁰ are taken together and form an oxo group; and

X¹ corresponds to just the side chain portion of amino acids and for each occurrence is independently selected from the side chain of the group of amino acids consisting of the D- or L- form, when applicable, of alanine, arginine, asparagine, aspartic acid, cysteine, cystine, glutamic acid, glutamine, glycine, histidine, hydroxylysine, hydroxyproline, isoleucine, leucine, lysine, methionine, phenylalanine, proline, serine, threonine, tryptophan, tyrosine, valine, β-alanine, β-lysine, α,α-dimethylglycine, α-aminobutyric acid, 4-hydroxyphenylglycine, phenylglycine, α,γ-diaminobutyric acid, ornithine and homoserine;

e is 0 or 1, provided that when e is 1 then X¹ corresponds to the side chain of β-lysine or β-alanine;

f is 0 or 1, provided that when f is 1 then X¹ corresponds to the side chain of β-lysine or β-alanine;

X² is H, alkyl having 1 to 4 carbons or benzyl;

Q is selected from the group consisting of H, OH, fluoro, chloro, bromo, iodo, OX³,

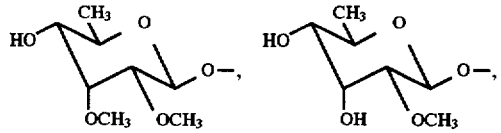

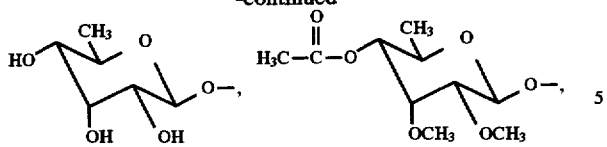

azetidin-1-yl, pyrrolidin-1-yl, piperidin-1-yl, 3,3-dimethylpiperidin-1-yl, hexahydroazepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino, 2,6-dimethylmorpholin-4-yl, thiomorpholino, and

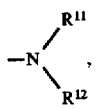

wherein $R^{11}$ and $R^{12}$ are independently selected from the group consisting of H, alkyl having 1 to 4 carbons, hydroxyalkyl having 2 to 4 carbons, cycloalkyl having 3 to 8 carbons, alkenyl having 3 or 4 carbons, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion; and $X^3$ is selected from the group consisting of optionally substituted alkyl having 1 to 4 carbons, optionally substituted cycloalkyl having 4 to 8 carbon atoms, and an optionally substituted aryl, aralkyl or heteroaryl group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl; wherein the optionally substituted alkyl and optionally substituted cycloalkyl can be substituted with 1 or 2 substituents independently selected from the group consisting of hydroxy, amino, N-alkylamino having 1 to 4 carbons, N,N-dialkylamino having a total of 2 to 6 carbons and alkoxy having 1 to 4 carbons; and where the optionally substituted aryl, aralkyl and heteroaryl groups are optionally substituted with 1 or 2 substituents independently selected from the group consisting of alkyl having 1 to 4 carbons, fluoro, chloro, bromo, acetyl, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido, sulfonamido, hydroxyalkyl having 1 to 4 carbons, aminoalkyl having 1 to 4 carbons, N-alkylaminoalkyl having 1 to 4 carbons in each of the alkyl portions, and N,N-dialkylaminoalkyl having a total of 2 to 6 carbons in the dialkylamino portion and 1 to 4 carbons in the alkyl portion;

provided that when $R^1$ or $R^2$ is a substituted alkyl or substituted cycloalkyl, then the hydroxy, alkoxy, fluoro, chloro, N-alkylamino, N,N-dialkylamino and amino substituents cannot be attached to the 1-position of said substituted alkyl or substituted cycloalkyl.

2. A compound according to claim 1, or a pharmaceutically acceptable salt thereof, wherein m is 1; $Z^1$ is H and Q is H or OH.

3. A compound according to claim 2 having the formula I, or a pharmaceutically acceptable salt thereof, wherein Q is H.

4. A compound according to claim 3, or a pharmaceutically acceptable salt thereof, wherein T is

wherein $Z^3$ is —$N(R^1R^2)$.

5. A compound according to claim 4, or a pharmaceutically acceptable salt thereof, wherein $R^1$ is H, methyl or optionally substituted alkyl having 2 to 6 carbons and $R^2$ is aminoalkyl having 2 to 6 carbons, N-alkylaminoalkyl having 1 to 4 carbons in the alkylamino portion and 2 to 4 carbons in the alkyl portion, N, N-dialkylaminoalkyl having a total of 2 to 6 carbons in the dialkylamino portion and 2 to 4 carbons in the alkyl portion or optionally substituted alkyl having 2 to 6 carbons;

wherein the optionally substituted alkyl is optionally substituted with

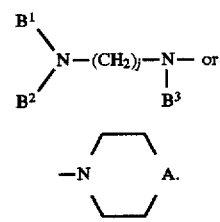

6. A compound according to claim 4, or a pharmaceutically acceptable salt thereof, wherein $R^1$ and $R^2$ are taken together with the nitrogen to which they are attached and form

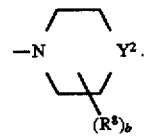

7. A compound according to claim 6, or a pharmaceutically acceptable salt thereof, wherein b is 0 and $Y^2$ is NH.

8. A compound according to claim 6, or a pharmaceutically acceptable salt thereof, wherein b is 1 and $Y^2$ is N, NH, CH or $CH_2$.

9. A compound according to claim 1, or a pharmaceutically acceptable salt thereof, wherein m is 2; $Z^1$ is H; Q is

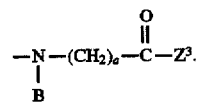

10. A compound according to claim 9, or a pharmaceutically acceptable salt thereof, wherein B is H or methyl and $Z^3$ is —$N(R^1R^2)$.

11. A compound according to claim 10, or a pharmaceutically acceptable salt thereof, wherein a is 1; $R^1$ is H, alkyl or aminoalkyl; and $R^2$ is aminoalkyl, N-alkylamino-alkyl having 1 to 4 carbons in the aminoalkyl portion and 2 to 4 carbons in the alkyl portion or N,N-dialkylaminoalkyl having a total of 2 to 6 carbons in the dialkylamino portion and 2 to 4 carbons in the alkyl portion.

12. A compound according to claim 10, or a pharmaceutically acceptable salt thereof, wherein a is 1 and $R^1$ and $R^2$ are taken together with the nitrogen to which they are attached and form piperazinyl.

13. A pharmaceutical composition comprising an effective amount of a compound of claim 1 and a pharmaceutically acceptable carrier or diluent.

14. A method of treating a bacterial infection in an animal in need thereof which comprises administering to said animal a bacterial treating amount of a compound of claim 1 or a pharmaceutically acceptable salt thereof.

15. A method of treating a mycoplasmic infection in an animal in need thereof which comprises administering to said animal a mycoplasmic treating amount of claim 1 or a pharmaceutically acceptable salt thereof.

* * * * *